United States Patent
D'Sidocky et al.

[11] Patent Number: 5,981,662
[45] Date of Patent: Nov. 9, 1999

[54] RUBBER COMPOUNDS CONTAINING POLYMERIC BIS-SUCCINIMIDE POLYSULFIDES

[75] Inventors: Richard Michael D'Sidocky, Ravenna; Lawson Gibson Wideman, Tallmadge, both of Ohio

[73] Assignee: The Goodyear Tire & Rubber Company, Akron, Ohio

[21] Appl. No.: 08/931,143

[22] Filed: Sep. 16, 1997

[51] Int. Cl.[6] .................................................. C08C 19/20
[52] U.S. Cl. ...................... 525/186; 525/189; 525/329.3; 525/330.4; 525/330.5; 525/331.1; 525/331.8; 525/332.7; 525/348; 152/450; 152/525; 152/564; 528/321
[58] Field of Search ....................... 525/348, 186, 525/189, 329.3, 330.4, 330.5, 331.1, 331.8, 332.7; 528/325; 152/450, 525, 564

[56] References Cited

U.S. PATENT DOCUMENTS

| | | | |
|---|---|---|---|
| 4,269,250 | 5/1981 | Harrison | 152/358 |
| 4,421,899 | 12/1983 | Yamazaki | 525/189 |

FOREIGN PATENT DOCUMENTS

| | | | |
|---|---|---|---|
| 9620246 | 7/1996 | European Pat. Off. | C08K 5/3415 |

OTHER PUBLICATIONS

Abstract 96–483926/48 Derwent

*Primary Examiner*—Patricia A. Short
*Attorney, Agent, or Firm*—Bruce J Hendricks

[57] ABSTRACT

The present invention relates to rubber compounds containing polymeric bis-succinimide polysulfides of the formula:

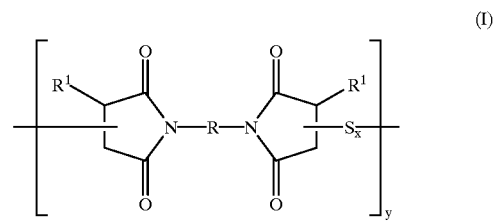

wherein R is selected from the group consisting of phenylene and xylylene; $R^1$ is selected from the group consisting hydrogen and alkyls having from 1 to 18 carbon atoms; x is an integer of from 2 to 8 and y is an integer of from 2 to 10.

11 Claims, No Drawings

RUBBER COMPOUNDS CONTAINING POLYMERIC BIS-SUCCINIMIDE POLYSULFIDES

BACKGROUND OF THE INVENTION

Monosuccinimide derivatives have been used as additives in the sulfur vulcanization of rubber. Such monosuccinimide derivatives are disclosed as imparting anti-reversion and antifatigue properties in the rubber. See CA 96-483926/48, Sep. 20, 1996.

PCT/EP95/05177, International Publication Number WO 96/20246 discloses sulfur-vulcanized rubber compositions containing bis-succinimide compounds. Use of these bis-succinimide compounds impart antireversion and/or accelerating properties in the rubber.

SUMMARRY OF THE INVENTION

The present invention relates compounds containing polymeric bis-succinimide polysulfides of the formula:

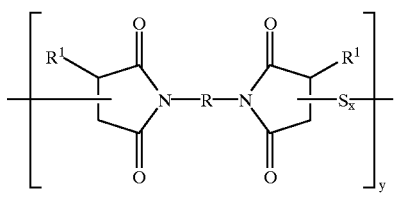

(I)

wherein R is selected from the group consisting of phenylene and xylylene; $R^1$ is selected from the group consisting hydrogen and alkyls having from 1 to 18 carbon atoms; x is an integer of from 2 to 8 and y is an integer of from 2 to 10.

DETAILED DESCPRIPTION OF THE PREFERRED EMBODIMENT

The present invention also relates to a vulcanized rubber composition comprising a sulfur-vulcanized rubber and from 0.1 to 10 phr of a polymeric bis-succinimide polysulfide of the formula:

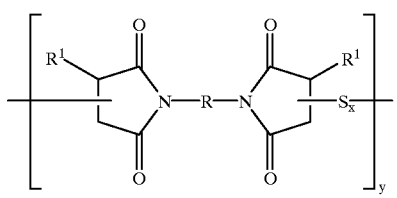

(I)

wherein R is selected from the group consisting of phenylene and xylylene; $R^1$ is selected from the group consisting hydrogen and alkyls having from 1 to 18 carbon atoms; x is an integer of from 2 to 8 and y is an integer of from 2 to 10.

The polysulfides used in the present invention may be present at various levels in the rubber compounds of the present invention. For example, the level may range from about 0.1 to 10.0 parts by weight per 100 parts by weight of rubber (also known as "phr"). Preferably, the level ranges from about 0.5 to about 5.0 phr.

The polysulfides may be prepared by reacting a suitable "imide" compound with sulfur. Representative of suitable "imide" compounds which may be used include N,N'-o-phenylenedicitraconamide;
N,N'-m-phenylenedicitraconamide;
N,N'-p-phenylenedicitraconamide;
N,N'-o-xylylenedicitraconamide;
N,N'-m-xylylenedicitraconamide;
N,N'-p-xylylenedicitraconamide; and the ortho, meta and para isomers of N,N'-phenylenedimethylmaleimide;
N,N'-xylylenedimethylmaleimide;
N,N'-phenylenediethylmaleimide;
N,N'-xylylenediethylmaleimide;
N,N'-phenylenedipropylmaleimide;
N,N'-xylylenedipropylmaleimide;
N,N'-phenylenedibutylmaleimide;
N,N'-xylylenedibutylmaleimide;
N,N'-phenylenedipentylmaleimide;
N,N'-xylylenedipentylmaleimide;
N,N'-phenylenedihexylmaleimide;
N,N'-xylylenedihexylmaleimide;
N,N'-phenylenediheptylmaleimide;
N,N'-xylylenediheptylmaleimide;
N,N'-phenylenedioctylmaleimide;
N,N'-xylylenedioctylmaleimide;
N,N'-phenylenedinonylmaleimide;
N,N'-xylylenedinonylmaleimide;
N,N'-phenylenedidecylmaleimide;
N,N'-xylylenedidecylmaleimide;
N,N'-phenylenediundecylmaleimide;
N,N'-xylylenediundecylmaleimide;
N,N'-phenylenedidodecylmaleimide;
N,N'-xylylenedidodecylmaleimide;
N,N'-phenyleneditridecylmaleimide;
N,N'-xylyleneditridecylmaleimide;
N,N'-phenylenedetetradecylmaleimide;
N,N'-xylyleneditetradecylmaleimide;
N,N'-phenylenedipentadecylmaleimide;
N,N'-xylylenedipentadecylmaleimide;
N,N'-phenylenedihexadecylmaleimide;
N,N'-xylylenedihexadecylmaleimide;
N,N'-phenylenediheptadecylmaleimide;
N,N'-xylylenediheptadecylmaleimide;
N,N'-phenylenedioctadecyl; and
N,N'-xylylenedioctadecylmaleimide.

The preferred imides are the N,N'-xylenedicitraconamides.

The imide is reacted with sulfur, $S_8$, under suitable conditions to form the polymeric bis-succinimide polysulfide. The imide may be reacted with sulfur in a variety of mole ratios. Generally, the mole ratio of the imide to the sulfur ranges from about 1:1 to about 1:10 with a range of from about 1:2 to about 1:4 being preferred.

In accordance with Formula I, x is an integer of from 2 to 8. Preferably, x is an integer of from 2 to 4. When a higher mole ratio of imide to sulfur is used, the lower integers for x are realized. When a lower mole ratio of imide to sulfur is used, the higher integers for x are realized.

In accordance with Formula I, y is an integer of from 2 to 10. The term "polymeric" is used herein to describe the "polymeric" bis-succinimide polysulfides where y is at least 2 (namely, the unit defined within the brackets of Formula I), repeat at least twice with a sulfur bridge ($S_2$ to $S_8$), linking the repeating units. Preferably, y is from 2 to 4. The reaction conditions conducive to producing polysulfides where y is a lower integer are shorter reaction times and lower reaction temperatures. The reaction conditions conducive to producing polysulfides when y is a higher integer are longer reaction times and higher reaction temperatures.

An organic solvent may be used to dissolve the imide. The solvent is preferably inert to the reaction between the imide and the sulfur. Illustrative of solvents suitable for use in the practice of this invention include: saturated and aromatic hydrocarbons, e.g., hexane, octane, dodecane, naphtha, decalin, tetrahydronaphthalene, kerosene, mineral oil, cyclohexane, cycloheptane, alkyl cycloalkane, benzene, toluene, xylene, alkylnaphthalene, and the like; acetone; ethers such as tetrahydrofuran, tetrahydropyran, diethylether, 1,2-dimethoxybenzene, 1,2-diethoxybenzene, the mono- and dialkylethers of ethylene glycol, propylene glycol, butylene glycol, diethylene glycol, dipropylene glycol, oxyethyleneoxypropylene glycol, and the like; fluorinated hydrocarbons that are inert under the reaction conditions such as perfluoroethane, monofluorobenzene, and the like. Another class of solvents are sulfones such as dimethylsulfone, diethylsulfone, diphenolsulfone, sulfolane, and the like. Mixtures of the aforementioned solvents may be employed so long as they are compatible with each other under the conditions of the reaction and will adequately dissolve the imide compound and not interfere with the reaction.

The reaction between the imide and the sulfur to form the polymeric bis-succimide polysulfides may be conducted over a wide temperature range. The temperature may range from moderate to an elevated temperature. In general, the reaction may be conducted at a temperature of between about 50° C. to 200° C. The preferred temperature range is from about 120° C. to 150° C., while the most preferred temperature range is from about 135° C. to 145° C.

The reaction pressure to form the polymeric bis-succimide polysulfides is not deemed to be critical. Pressures ranging from about 0 kPa to 689 kPa may be used.

The process for the preparation of the polymeric bis-succimide polysulfides may be carried out in a batch, semi-continuous or continuous manner. The reaction may be conducted in a single reaction zone or in a plurality or reaction zones, in series or in parallel. The reaction may be conducted intermittently or continuously in an elongated tubular zone or in a series of such zones. The material of construction of the equipment should be such as to be inert during the reaction. The equipment should also be able to withstand the reaction temperatures and pressures. The reaction zone can be fitted with internal and/or external heat exchangers to control temperature fluctuations. Preferably, an agitation means is available to ensure the uniform reaction. Mixing induced by vibration, shaker, stirrer, rotating, oscillation, etc. are all illustrative of the types of agitation means which are contemplated for use in preparing the composition of the present invention. Such agitation means are available and well known to those skilled in the art.

Use of the polymeric bis-succinimide polysulfides improve the rheometer antireversion properties of "sulfur-vulcanized elastomers or rubbers." The term "sulfur-vulcanized elastomer or rubber" as used herein embraces both vulcanized forms of natural and all its various raw and reclaim forms as well as various synthetic rubbers. The synthetic elastomers include conjugated diene homopolymers and copolymers and copolymers of at least one conjugated diene and aromatic vinyl compound. Representative synthetic polymers include the homopolymerization products of butadiene and its homologues and derivatives, as for example, methyl-butadiene, dimethylbutadiene and pentadiene as well as copolymers, such as those formed from butadiene or its homologues or derivatives with other unsaturated organic compounds. Among the latter are acetylenes, for example, vinyl acetylene; olefins, for example, isobutylene, which copolymerizes with isoprene to form butyl rubber; vinyl compounds, for example, acrylic acid, acrylonitrile (which polymerizes with butadiene to form NBR), methacrylic acid and styrene, the latter polymerizing with butadiene to form SBR, as well as vinyl esters and various unsaturated aldehydes, ketones and ethers, e.g. acrolein, methyl isopropenyl ketone and vinylethyl ether. Also included are the various synthetic rubbers prepared by the homopolymerization of isoprene and the copolymerization of isoprene and other diolefins in various unsaturated organic compounds. Also included are the synthetic rubbers such as 1,4-cis-polybutadiene and 1,4-cis-polyisoprene and similar synthetic rubbers.

Specific examples of synthetic rubbers include neoprene (polychloroprene), polybutadiene (including trans- and cis-1,4-polybutadiene), polyisoprene (including cis-1,4-polyisoprene), butyl rubber, copolymers of 1,3-butadiene or isoprene with monomers such as styrene, acrylonitrile and methyl methacrylate as well as ethylene/propylene terpolymers, also known as ethylene/propylene/diene monomer (EPDM) and, in particular, ethylene/propylene/dicyclopentadiene terpolymers and styrene/isoprene/butadiene rubber. The preferred synthetic rubbers for use in the present invention are polybutadiene, polyisobutylene, butadiene-styrene copolymers and cis, 1,4-polyisoprene.

Vulcanization of the rubber compound of the present invention is generally carried out at conventional temperatures ranging from about 100° C. and 200° C. Preferably, the vulcanization is conducted at temperatures ranging from about 110° C. to 180° C. Any of the usual vulcanization processes may be used such as heating in a press or mold, heating with superheated steam or hot air or in a salt bath.

In addition to the polymeric bis-succinimide polysulfides, other rubber additives may also be incorporated in the rubber compound. The additives commonly used in rubber vulcanizates are, for example, carbon black, tackifier resins, processing aids, antioxidants, antiozonants, stearic acid, activators, waxes, phenol-formaldehyde resins, oils and peptizing agents. As known to those skilled in the art, depending on the intended use of the rubber compound, certain additives mentioned above are commonly used in conventional amounts. Typical additions of carbon black comprise about 20 to 100 parts by weight of diene rubber (phr), preferably 30 to 80 phr. Typical amounts of tackifier resins comprise about 1 to 5 phr. Typical amounts of antioxidants comprise 1 to about 10 phr. Typical amounts of antiozonants comprise 1 to about 10 phr. Typical amounts of stearic acid comprise 1 to about 2 phr. Typical amounts of zinc oxide comprise 2 to 5 phr. Typical amounts of waxes comprise 1 to 5 phr. Typical amounts of phenol-formaldehyde resins comprise 1 to 8 phr. Typical amounts of oils comprise 5 to 40 phr. Typical amounts of peptizers comprise 0.1 to 1 phr. The presence and relative amounts of the above additives are not an aspect of the present invention.

The vulcanization of the rubber compound is conducted in the presence of a sulfur-vulcanizing agent. Examples of suitable sulfur-vulcanizing agents include elemental sulfur (free sulfur) or sulfur donating vulcanizing agents, for example, an amine disulfide, polymeric polysulfide or sulfur olefin adducts. Preferably, the sulfur-vulcanizing agent is elemental sulfur. As known to those skilled in the art, sulfur-vulcanizing agents are used in an amount ranging from about 0.5 to 8 phr with a range of from 1.0 to 2.25 being preferred.

Accelerators are conventionally used to control the time and/or temperature required for vulcanization and to improve the properties of the vulcanizate. In some instances, a single accelerator system may be used, i.e., primary accelerator. Conventionally, a primary accelerator is used in amounts ranging from about 0.5 to 2.0 phr. In another instance, combinations of two or more accelerators may be used which may consist of a primary accelerator which is generally used in the large amount (0.5 to 2.0 phr), and a secondary accelerator which is generally used in smaller amounts (0.01–0.50 phr) in order to activate and to improve the properties of the vulcanizate. Combinations of these accelerators have been known to produce a synergistic effect of the final properties and are somewhat better than those produced by use of either accelerator alone. In addition, delayed action accelerators may be used which are not affected by normal processing temperatures but produce satisfactory cures at ordinary vulcanization temperatures. Suitable types of accelerators that may be used include amines, disulfides, guanidines, thiophthalimides, thioureas, thiazoles, thiurams, sulfenamides, dithiocarbamates and xanthates. Preferably, the primary accelerator is a sulfenamide. If a secondary accelerator is used, the secondary accelerator is preferably a guanidine, dithiocarbamate or thiuram compound.

The rubber compounds containing the polymeric bis-succinimide polysulfides may be used in the preparation of and, therefore, in the form of composite products including tires, power belts, conveyor belts, printing rolls, rubber shoe heels and soles, rubber wringers, automobile floor mats, mud flaps for trucks, ball mill liners, and the like. Preferably, the rubber vulcanizates are used in sidewall, tread, carcass ply, wirecoat or overlay compounds for tires.

The following examples are presented in order to illustrate but not limit the present invention.

EXAMPLE 1

Poly N,N'-m-Xylylenebis(3-methylsuccinimide) Polysulfide

A 1-liter, round-bottom flask was charged with 32.4 g (0.10 mole) of N,N'-m-xylylenedicitraconimide, 25.6 g (0.80 mole) of sulfur ($S_8$) and 400 ml of mixed xylenes. The system was heated to reflux under an atmospheres of nitrogen for 13 hours with a pot temperature of 141–142° C. The reaction mixture was cooled overnight to give 13.6 g of sulfur, which was removed by suction filtration. The solvent was removed under reduced pressure to give 46.2 g of the orange-yellow solid product melting at 50–55° C. and giving an infrared spectrum showing loss of imide double bond character, with increases in aliphatic C—H stretching vibrations and polysulfide formation. Small molecule GPC analysis shows polymeric polysulfides and sulfur weight pickup plus sulfur analysis gives x as averaging 3.75 sulfurs in the polymeric polysulfides.

EXAMPLE 2

Poly N,N'-m-Xylylenebis(3-methylsuccimimide) Polysulfide

A reaction was carried out under the conditions of Example 1, except the reflux under nitrogen was limited to four hours before cooling overnight. Suction filtering gave 16.8 g of sulfur. Solvent removal gave 44.4 g of the orange-yellow solid melting at 55–60° C. and giving an infrared spectrum showing decrease of imide double bond character and increases in polysulfide and aliphatic hydrocarbon character. Small molecular GPC analysis shows polymeric polysulfides and sulfur weight pickup plus sulfur analysis gives x as averaging 2.75.

EXAMPLE 3

Physical Testing

Table I below shows the basic rubber compound that was used in this example. The rubber compound was prepared in a three-stage Banbury mix. All parts and percentages are by weight unless otherwise noted. The cure data as well as other physical data for each sample are listed in Tables II and III. In Table III, the various properties are reported for samples which were cured for 20 minutes and 90 minutes at 150° C., 6 minutes and 28 minutes at 170° C.

TABLE I

| | Sample No. | | |
|---|---|---|---|
| | Control Sample 1 | Sample 2 | Sample 3 |
| 1st Non-Productive | | | |
| Natural Rubber | 100 | 100 | 100 |
| Carbon Black | 30 | 30 | 30 |
| Oil | 5 | 5 | 5 |
| 2nd Non-Productive | | | |
| Stearic Acid | 2 | 2 | 2 |
| Zinc Oxide | 3 | 3 | 3 |
| Carbon Black | 10 | 10 | 10 |
| Productive | | | |
| N-cyclohexyl benzothiazole-2-sulfenamide | 1.0 | 1.0 | 1.0 |
| N-(cyclohexylthio)phthalimide | 0.1 | 0.1 | 0.1 |
| Amine Antioxidant | 0.75 | 0.75 | 0.75 |
| Sulfur | 2.25 | 2.25 | 2.25 |
| poly-N,N'-m-xylylenebis (3-methylsuccinimide)polysulfide 3.75 moles of sulfur/polymeric bridge | 0 | 2.0 | 0 |
| poly-N,N'-m-xylylenebis (3-methylsuccinimide) polysulfide 2.75 moles of sulfur/polymeric bridge | 0 | 0 | 2.0 |
| Total | 154.1 | 156.1 | 156.1 |

Cure properties were determined using a Monsanto oscillating disc rheometer which was operated at a temperature of 150° C. and at a frequency of 11 hertz. A description of oscillating disc rheometers can be found in the Vanderbilt Rubber Handbook edited by Robert O. Ohm (Norwalk, Conn., R. T. Vanderbilt Company, Inc., 1990), pages 554–557. The use of this cure meter and standardized values read from the curve are specified in ASTM D-2084. A typical cure curve obtained on an oscillating disc rheometer is shown on page 555 of the 1990 edition of the Vanderbilt Rubber Handbook.

In such an oscillating disc rheometer, compounded rubber samples are subjected to an oscillating shearing action of constant amplitude. The torque of the oscillating disc embedded in the stock that is being tested that is required to oscillate the rotor at the vulcanization temperature is measured. The values obtained using this cure test are very significant since changes in the rubber or the compounding recipe are very readily detected.

The following tables report cure properties that were determined from cure curves that were obtained for the three rubber formulations that were prepared. These properties include torque maximum (Max Tq), torque minimum (Min Tq), time to MAX Tq, delta torque (DEL Tq), minutes to 1 point of the torque increase (T1), minutes to 25 percent of the torque increase (T25) and minutes to 90 percent of the torque increase (T90).

Cure reversion measured using a rheometer can be defined as the incremental time required for a fixed decrease in torque from the maximum value, expressed here for example as Smax-1pt (time for the torque to decrease 1.0 unit or point below the maximum value Max Tq). Such cure reversion measurements are defined by G M Bristow (NR Technology, 17 (1) 7, 1986).

Shore Hardness was determined in accordance with ASTM-1415.

In Table III, the various properties of the samples are reported which were cured for 20 minutes at 150° C., 90 minutes at 150° C., 6 minutes at 170° C. or 28 minutes at 170° C.

Table II compares the reversion-resistant behavior at 150° C. and 170° C., respectively, for the poly-N-N'-m-xylylenebis(3-methylsuccinimide)polysulfides of the present invention (Samples 2 and 3) versus (Control Sample 1) which has no poly-N-N'-m-xylylenebis(3-methylsuccinimide)polysulfides added to the compound formulation of Table I. It is immediately obvious when examining Table II (150° C. cure) and (170° C. cure) that the poly-N,N'-m-xylylenebis(3-methylsuccinimide)polysulfides (Samples 2 and 3) provide excellent reversion-resistant behavior when compared to Control Sample 1 which has no poly-N,N'-m-xylylenebis(3-methylsuccinimide)polysulfides added to the compound formulation. At the 150° C. cure temperature, Control Sample 1 had a maximum reversion of −10.2 pts while the poly-N,N'-m-xylylenebis(3-methylsuccinimide)polysulfides (Samples 2 and 3) showed maximum reversions of only −3.5 pts, respectively. Comparison of reversion behavior at 170° C. likewise shows the reversion-resistant superiority of the poly-N,N'-m-xylylenebis(3-methylsuccinimide)polysulfides (Samples 2 and 3) of the present invention. Thus, while Control Sample 1 had a maximum reversion of −14.5 pts, the poly-N,N'-m-xylylenebis(3-methylsuccinimide)polysulfides (Samples 2 and 3) showed a maximum reversion of only −7.0 pts and −6.5 pts, respectively.

From the results of Table III, it is clear that the poly-N, N'-m-xylylenebis(3-methylsuccinimide)polysulfides also provided improved properties to the final vulcanizate. The poly-N,N'-m-xylylenebis(3-methylsuccinimide)polysulfides of the present invention showed improvements in retention of modulus during overcure and with increasing cure temperature, improvements in retention of tensile strength, improvements in retention of hardness and improvements in retention of rebound properties. Reduction in heat buildup along with extended times to sample failure or no failure at all was also observed for Goodrich Blowout testing when the poly-N,N'-m-xylylenebis(3-methylsuccinimide) polysulfides were utilized as part of the compound formulation.

TABLE II

| | Sample No. | | |
|---|---|---|---|
| | Control Sample 1 | Sample 2 | Sample 3 |
| Rheometer @ 150° C. | | | |
| Max Tq (DN.M) | 40 | 40 | 40 |
| Min Tq (DN.M) | 6 | 6.5 | 6.5 |
| Time to Max Tq (min) | 18 | 15 | 15 |
| Del Tq (DN.M) | 34 | 33.5 | 33.5 |
| T1 pt Rise, Min | 4.5 | 2.5 | 2.8 |
| T25 (Min) | 7.5 | 3.5 | 4.0 |
| T90 (Min) | 11.5 | 8 | 8 |
| Reversion (min/pt drop) | | | |
| Smax-1 pt | 6 | 9 | 10 |
| Smax-2 pt | 13 | 18 | 18 |
| Smax-3 pt | 20 | 36 | 34 |

TABLE II-continued

| | Sample No. | | |
|---|---|---|---|
| | Control Sample 1 | Sample 2 | Sample 3 |
| Smax-4 pt | 28 | | |
| Smax-5 pt | 35 | | |
| Smax-6 pt | 45 | | |
| Smax-7 pt | 58 | | |
| Smax-8 pt | 74 | | |
| Smax-9 pt | 102 | | |
| Maximum Reversion/Time | | | |
| Pt drop | −9 | −3.5 | −3.5 |
| Time (min) | 10.2 | 65 | 51 |
| Rheometer @ 170° C. | | | |
| Max Tq (DN.M) | 36.5 | 37 | 37 |
| Min Tq (DN.M) | 5 | 5 | 5 |
| Time to Max Tq (min) | 4.5 | 5 | 5 |
| Del Tq (DN.M) | 31.5 | 32 | 32 |
| T25 (Min) | 2 | 1.8 | 2 |
| T90 (Min) | 3.3 | 3 | 3.5 |
| Reversion (min/pt drop) | | | |
| Smax-1 pt | 2 | 2 | 1.5 |
| Smax-2 pt | 3 | 3 | 2.5 |
| Smax-3 pt | 4 | 4.5 | 4 |
| Smax-4 pt | 5.5 | 6 | 5.5 |
| Smax-5 pt | 7 | 8 | 7.5 |
| Smax-6 pt | 8 | 11 | 11 |
| Smax-7 pt | 10 | 21 | |
| Smax-8 pt | 12 | | |
| Smax-9 pt | 14.5 | | |
| Smax-10 pt | 17.5 | | |
| Smax-11 pt | 22.5 | | |
| Smax-12 pt | 28.5 | | |
| Smax-13 pt | 39.5 | | |
| Smax-14 pt | 62.5 | | |
| Maximum Reversion/Time | | | |
| Pt drop | −14.5 | −7 | −5.5 |
| Time (min) | 115.5 | 21 | 18 |

TABLE III

| | Sample No. | | |
|---|---|---|---|
| | Control Sample 1 | Sample 2 | Sample 3 |
| 300% Modulus | | | |
| 20'/150° C. (MPa) | 14.18 | 13.13 | 13.28 |
| 90'/150° C. (MPa) | 10.02 | 11.92 | 12.62 |
| 6'/170° C. (MPa) | 12.23 | 11.65 | 11.52 |
| 28'/170° C. (MPa) | 7.25 | 9.2 | 9.79 |
| Tensile Strength | | | |
| 20'/150° C. (MPa) | 22.77 | 22.55 | 22.47 |
| 90'/150° C. (MPa) | 18.53 | 19.15 | 20.47 |
| 6'/170° C. (MPa) | 22.88 | 22.26 | 22.36 |
| 28'/170° C. (MPa) | 13.94 | 18.03 | 17.73 |
| Elongation at Break | | | |
| 20'/150° C. (%) | 459 | 473 | 468 |
| 90'/150° C. (%) | 482 | 445 | 454 |
| 6'/170° C. (%) | 497 | 503 | 505 |
| 28'/170° C. (%) | 484 | 497 | 463 |
| Shore A Hardness (Room Temperature) | | | |
| 20'/150° C. | 62.3 | 61.2 | 61.7 |
| 90'/150° C. | 57 | 61.3 | 61.3 |
| 6'/170° C. | 59.9 | 60.7 | 59.1 |
| 28'/170° C. | 51 | 55.9 | 56.7 |

TABLE III-continued

| | Sample No. | | |
|---|---|---|---|
| | Control Sample 1 | Sample 2 | Sample 3 |
| Shore A Hardness (100° C.) | | | |
| 20'/150° C. | 56.9 | 56 | 56.1 |
| 90'/150° C. | 49.3 | 54.5 | 55 |
| 6'/170° C. | 53.8 | 54 | 52.8 |
| 28'/170° C. | 42.9 | 50.2 | 59.7 |
| Rebound (Room Temp) | | | |
| 20'/150° C. (%) | 57.5 | 57 | 57.1 |
| 90'/150° C. (%) | 51.7 | 52.6 | 54.2 |
| 6'/170° C. (%) | 56.3 | 54.6 | 54.6 |
| 28'/170° C. (%) | 48 | 50.7 | 51.2 |
| Rebound (100° C.) | | | |
| 20'/150° C. (%) | 71.9 | 72.6 | 72.8 |
| 90'/150° C. (%) | 64.1 | 65.8 | 67.9 |
| 6'/170° C. (%) | 70.1 | 69.4 | 69.8 |
| 28'/170° C. (%) | 56.3 | 62.9 | 62.8 |
| Goodrich Blow Out (ASTM D623) | | | |

Stroke 6.35 mm    Cyclic comp 800.00 1/min
Load on Sample    20.18 kg
Preheat tmp 93° C.  Preheat time 15.00 min
Stop Cond:        Time to Blow out or 60 min
Fail Time (Min)

| | | | |
|---|---|---|---|
| 20'/150° C. | 13 | no failure | no failure |
| 90'/150° C. | 12 | no failure | no failure |
| 6'/170° C. | 15 | 42 | no failure |
| 28'/170° C. | 2 | no failure | no failure |
| Max Temp Rise (° C.) | | | |
| 20'/150° C. | 150.0 | 125.5 | 122.2 |
| 90'/150° C. | 151.7 | 125.5 | 123.9 |
| 6'/170° C. | 147.7 | 173.9 | 132.2 |
| 28'/170° C. | 121.1 | 125.5 | 123.9 |

What is claimed is:

1. A vulcanized rubber composition comprising a sulfur-vulcanized rubber and from 0.1 to 10 phr of a polymeric bis-succinimide polysulfide of the formula:

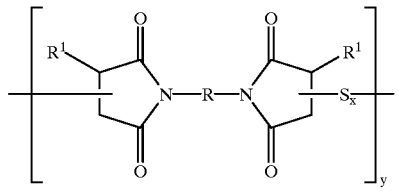

(I)

wherein R is selected from the group consisting of phenylene and xylylene; $R^1$ is selected from the group consisting hydrogen and alkyls having from 1 to 18 carbon atoms; x is an integer of from 2 to 8 and y is an integer of from 2 to 10.

2. The rubber composition of claim 1 wherein said rubber is selected from the group consisting of a natural rubber and synthetic elastomer selected from conjugated diene homopolymers and copolymers and from copolymers of at least one conjugated diene and aromatic vinyl compound.

3. The rubber composition of claim 2 wherein said rubber is selected from the group consisting of natural rubber, polychloroprene, synthetic 1,4-cis-polyisoprene, butyl rubber, polybutadiene, styrene-butadiene copolymer, isoprene-butadiene copolymer, styrene-isoprene-butadiene rubber, methyl methacrylate-butadiene copolymer, isoprene-butadiene copolymer, methyl methacrylate-isoprene copolymer, acrylonitrile-isoprene copolymer, acrylonitrile-butadiene copolymer, and mixtures thereof.

4. The rubber composition of claim 1 wherein from 0.5 to about 5.0 phr of said polymeric bis-succinimide polysulfide is present.

5. The rubber composition of claim 1 wherein R is xylylene.

6. The rubber composition of claim 1 wherein the R is phenylene.

7. The rubber composition of claim 1 wherein $R^1$ is an alkyl having 1 carbon atom.

8. The rubber composition of claim 1 in the form of a composite product.

9. The rubber composition of claim 8 wherein said composite product is selected from the group consisting of tires, power belts, conveyor belts, printing rolls, rubber shoe heels and soles, rubber wringers, automobile floor mats, mud flaps and ball mill liners.

10. The rubber composition of claim 9 wherein said composite product is a tire.

11. The rubber composition of claim 10 wherein said rubber composition is used as sidewall, carcass ply, wirecoat or overlay compounds.

* * * * *